US008425843B2

(12) United States Patent
Ciotti et al.

(10) Patent No.: US 8,425,843 B2
(45) Date of Patent: Apr. 23, 2013

(54) INTEGRATED APPARATUS AND METHOD TO DETECT INFLAMMATORY STATES PRESENT IN A SAMPLE OF WHOLE BLOOD

(75) Inventors: Alfredo Ciotti, Udine (IT); Paolo Galiano, Padua (IT)

(73) Assignee: Alifax Holding SpA, Polverara (IT)

(*) Notice: Subject to any disclaimer, the term of this patent is extended or adjusted under 35 U.S.C. 154(b) by 808 days.

(21) Appl. No.: 12/373,012

(22) PCT Filed: Jul. 13, 2007

(86) PCT No.: PCT/EP2007/057223
§ 371 (c)(1),
(2), (4) Date: Jan. 8, 2009

(87) PCT Pub. No.: WO2008/006897
PCT Pub. Date: Jan. 17, 2008

(65) Prior Publication Data
US 2009/0311736 A1    Dec. 17, 2009

(30) Foreign Application Priority Data
Jul. 14, 2006   (IT) .................. UD06A0177

(51) Int. Cl.
*G01N 33/00* (2006.01)
*C12Q 1/02* (2006.01)
*C12M 1/34* (2006.01)
*C12M 3/00* (2006.01)
*G01N 33/86* (2006.01)

(52) U.S. Cl.
USPC ......... 422/73; 435/29; 435/287.2; 435/287.3; 435/288.7; 436/70

(58) Field of Classification Search ............... 422/73; 435/29, 287.2, 287.3, 288.7; 436/70
See application file for complete search history.

(56) References Cited

U.S. PATENT DOCUMENTS

| 5,506,145 A | 4/1996 | Bull et al. |
| 5,827,746 A * | 10/1998 | Duic ............................ 436/70 |
| 6,632,679 B1 * | 10/2003 | Breda .......................... 436/70 |
| 2002/0115222 A1 * | 8/2002 | Spillert et al. ................ 436/70 |
| 2003/0022382 A1 | 1/2003 | Negersmith |
| 2004/0065143 A1 | 4/2004 | Husher |

FOREIGN PATENT DOCUMENTS

| EP | 0 822 412 | 2/1998 |
| EP | 1 098 188 | 5/2001 |
| IT | UD2006A000111 | 4/2006 |

(Continued)

OTHER PUBLICATIONS

Urdal et al. "Rapid Immunometric Measurement of C-Reactive Protein in Whole Blood". *Clinical Chemistry*, vol. 38, No. 4, pp. 580-574 (1992).
Plebani et al. "Mistakes in a stat laboratory: types and frequency". *Clinical Chemistry*, vol. 43, No. 8, pp. 1348-1351 (1997).

*Primary Examiner* — Sam P Siefke
*Assistant Examiner* — Bryan Kilpatrick
(74) *Attorney, Agent, or Firm* — Hamre, Schumann, Mueller & Larson, P.C.

(57) ABSTRACT

Integrated apparatus and method for hematological analyses, wherein the apparatus, comprises, arranged substantially in line and integrated substantially in a single machine, a device (14) of the optical type to detect substantially instantaneously the speed of blood sedimentation (ESR) by measuring the optical density, or absorbance, of the blood sample, and a measuring assembly (18) with a cell-counter function or suchlike.

21 Claims, 4 Drawing Sheets

FOREIGN PATENT DOCUMENTS

| | | |
|---|---|---|
| WO | WO 89/06801 | 7/1989 |
| WO | WO 90/08949 | 8/1990 |
| WO | WO 92/11537 | 7/1992 |
| WO | WO 2005/022125 | 3/2005 |

* cited by examiner fig.1 fig. 2 fig. 3 fig. 4 fig. 5 fig. 6

INTEGRATED APPARATUS AND METHOD TO DETECT INFLAMMATORY STATES PRESENT IN A SAMPLE OF WHOLE BLOOD

FIELD OF THE INVENTION

The present invention concerns an integrated apparatus for detecting inflammatory states present in a sample of whole blood, and the relative method. In particular, the integrated apparatus according to the present invention is able to perform a plurality of analyses of the physical type, such as measuring the erythrocyte sedimentation rate ESR, of the immunological type and coagulative type, using a single sample of whole blood.

BACKGROUND OF THE INVENTION

It is known that, in order to ascertain a possible pathology, diagnostic tests are used, and according to the results of these, the most appropriate therapy is begun.

In a clinical laboratory, at least three different pre-analytical protocols are normally provided, which use three different blood samples, collected in three different containers, so that at least three different groups of clinical tests can be carried out.

A first group of tests comprises physical tests to measure the erythrocyte sedimentation rate in the blood (ESR), for example using the method and apparatus described in the European patent application EP-A-1.098.188 (EP'188) in the name of the present Applicant, and to effect measurements of size of the corpuscular part of the blood, and also to determine values of anemia and hematocrit and/or hemoglobin, as described in the Italian patent application UD2006000111 in the name of the present Applicant.

The test to measure the ESR is indicative, non-specifically, of the presence of an inflammatory state, since it is known that, in particular pathological states, the red corpuscles tend to aggregate and form agglomerations, called rouleaux. This is typically shown by the ESR clinical test which has the advantage of being easy to carry out and inexpensive.

Aggregation is normally impeded by the negative charge of the red corpuscles, as a result of which the latter repel each other. However, it is possible that the negative charge may be neutralized when there are proteins with a positive charge present in the plasma, which therefore promote aggregation.

This explains the increase in the ESR in physiological or pathological situations which imply an increase in fibrinogen, beta globulins, alpha globulins and gamma globulins.

In collagen pathologies, rheumatic diseases and Hodgkin's disease, there is a connection between the ESR values and the level of activity of the disease: the ESR exam, in these cases, is a useful instrument for monitoring a patient's clinical conditions.

From the above, it is clear that the ESR indirectly reveals a state of phlogosis.

It is also clear that the non-specific nature of the ESR test makes it necessary to use it in the context of clinical and anamnestic data, which retain a primary role.

Therefore, when the ESR value exceeds normal values, it is consolidated practice to carry out other diagnostic tests, even if they are more expensive, but which are more specific.

Among these, a second group of tests, of the immunological type, that is, based on an antigen-antibody reaction, serves to assess the concentration of C-reactive protein (CRP), streptococcus infections (ASO) and the rheumatic factor RF.

The C-reactive protein CRP is a protein, present in the blood serum, which significantly increases following damage to the tissues, bacterial and viral infections, cardiac pathologies and malign neoplasia.

Recent years have seen important developments in the search for inflammatory markers which could act as predictors of the risk of cardiovascular events; the most credited hypothesis is that atherosclerosis is the result of an inflammatory process, which develops in response to metabolic damage (diabetes, hypercholesterolemia), physical damage (hypertension) or behavioral damage (smoking).

The clinical implications of measuring these markers consist in the possibility of evaluating the individual risk of cardiovascular events. The estimation of traditional predisposing factors (advanced age, diabetes, smoking, hypertension, hyperlipemia and previous angina) defines the risk on a population level quite accurately, but allows to predict only 50-60% of the variation in the absolute risk in the individual patient.

The importance has thus emerged of ascertaining the values of C-reactive protein as predictors of independent risk.

Known methods to determine CRP use the fact that, in a solution, an antibody recognizes and binds to a specific antigen, determining an immunological reaction that is detected in particular by observing the change in optical properties of the solution.

To exploit this effect and effectively investigate it by measuring the change in optical properties, the formation of a suspension or a precipitate has to be avoided, the formation of an aggregation or an agglutination being, vice versa, desirable.

In particular, in suitable conditions an immunological reaction can occur between specific antibodies immobilized on a suitable carrier, for example gold colloid or latex particles, and the antigens, the result of which is an aggregation or agglutination mixture that can be determined in its change in absorbance or other optical properties.

The standard test to determine CRP consists in measuring the level of turbidity caused by the agglutination due to the mixing of a determinate quantity of blood serum or plasma with latexes consisting of balls, mainly polystyrene, with an average diameter of about 0.120 micron, covered with an anti-CRP antibody and dispersed or diluted in particular liquids, called buffers.

The CRP test used in the state of the art is based on nephelometry and requires average times of about 6 minutes to achieve significant kinetics, since the nephelometric technique requires low-concentration reagents.

Other methods are disclosed, for example in the documents WO-A-89/06801 and WO-A-92/11537, that are based on gold colloid that forms superaggregated complexes, that may replace the latex particles used in immunoagglutination assay, detectable by a densitometer or a reflectometer.

Further methods use whole blood, instead of blood serum or plasma, and provide an initial lysis of the red corpuscles present and then agglutination due to the antigen present in the volume of the plasma, which meets the CRP-specific antibody present in the sensitized carrier. In this case, the value of the CRP measured is corrected with the hematocrit value of the whole blood sample.

A known method is described, for example, in the document "Rapid Immunometric Measurement of C-Reactive Protein in Whole Blood", Petter Urdal, Stig M. Borch, Sverre Landaas, May B. Krutnes, Geir O. Gogstad, and Per Hjortdahl, published in Clinical Chemistry 38/4, 580-584 (1992).

In particular, this latter is related to the aforementioned documents WO-A-89/06801 and WO-A-92/11537 and it discloses an immunoassay method, commercially available as a kit called "NycoCard CRP Whole Blood test", to determine the content of C-reactive protein (CRP) in a sample of whole blood that involves an immobilization of a CRP specific antibody onto a ultrasmall gold colloid that acts as a suitable carrier, a lysis treatment on the sample of whole blood, an immunological reaction between antigen and immobilized antibody and an investigation of the resulting aggregation or agglutination deriving from the gold colloid carrying the antibodies bound to the antigens, using a reflectometer.

From the European patent application EP-A-0.822.412 (EP'412) an immunoassay method is also known for detecting the content of C-reactive protein (CRP) in a whole blood sample that, as well as in the aforementioned document "Rapid Immunometric Measurement of C-Reactive Protein in Whole Blood", involves an agglutination reaction in the sample between antigen and antibody immobilized on a polystyrene latex and an optical measurement of the change of absorbance of the agglutination mixture, wherein the whole blood sample is forcibly lysed.

In the course of infections produced by *Streptococcus pyogenes*, numerous substances are secreted, including two hemolysins: Streptolysin "O" and Streptolysin "S". Streptolysin "O" is a toxin able to stimulate the production of specific antibodies. With the same principle of the CRP test immunological reactions are achieved for the quantitative determination of the anti_Streptolysin "O" antibodies, ASO tests.

The discovery of these antibodies has been very useful in order to diagnose streptococcal infections and the relative consequences associated with them, such as rheumatic fever and acute glomerulonephritis. The test is based on the reaction between the antibody and the particles of latex linked to Streptolysin "O". The ASO values are determined kinetically according to a calibration curve made using a sample with a known ASO concentration according to a succession of scalar concentrations, using the techniques already known in the CRP test.

Furthermore, a test is made in order to quantify the rheumatic factor RF, which is a macroglobulin which agglutinates particles of latex sensitized with human gamma globulins, and can be found in most patients affected with evolutive polyarthritis. The latex agglutination test allows to differentiate this illness from articular rheumatism or rheumatic fever, where the rheumatoid factor is not present.

A third group of tests concerns coagulation and, in particular, the evaluation of the concentration of fibrinogen present in the blood. Coagulation depends on factors found in the plasma and the platelets, thrombin, prothrombin, thromboplastin.

The level of fibrinogen in the blood can vary in pathological situations, for example increasing in inflammations, rheumatisms, inflammations of the connective tissues, in the lymphoma (more than 5 g/l), during pregnancy, in some cases of nephrosis and in the event of burns. On the contrary it decreases if too much of it is consumed (hyperfibrinogenolysis), in cases of kidney failure and disseminated intravascular coagulation due to various shocks (septic shock, prostate cancer).

For example, the International patent application WO-A-90/08949 (WO'949) discloses a plurality of optical based methods to determine the coagulation properties of a blood sample.

It is also known, as reported in a study published in Clinical Chemistry, "Mistakes in a stat laboratory: types and frequency", that the analytical flow of each clinical test has three main working steps, that is, a pre-analytical step, an analytical step and a post-analytical step.

According to this study, 68.2% of mistakes occur during the pre-analytical step, 13.3% during the analytical step and the remaining 18.5% during the post-analytical step.

It is also clear that the first and fundamental requirement that the clinic and the patient ask from those performing the analysis is the reliability of the analytical result.

From the International patent application WO-A-2005/022125 (WO'125) in the name of the present Applicant an integrated apparatus is also known that comprises, arranged in line and integrated in a single machine, a device of the optical type to detect the speed of blood sedimentation (ESR) of a blood sample and a measuring assembly with a cell-counter function. The apparatus comprises one or more containers suitable to be perforated by a pick-up needle, in order to pick up the sample to be analyzed, in a quantity of between 30 µl and 200 µl. The sample is sent, by means of a pump and trough a circuit, to the analytical devices.

Such an apparatus is directed to the analysis of simple physical properties of the blood sample and all the components are developed keeping this aim in mind, for example, it allows only a rough control of the dosage of the sample and of the quantity of the sample that is sent to the analytical devices, nor does it make a pre-treatment on the whole blood sample to prepare the same for the subsequent analysis.

One purpose of the present invention is to achieve an apparatus that allows to carry out a plurality of diagnostic tests, which use different reaction techniques and a single sample of whole blood which has been subjected to a single pre-analytical treatment, in order to achieve the various reaction phenomena to be studied, both physical, immunological and coagulative.

Another purpose is to perfect a method that intrinsically reduces the probabilities of error in the pre-analytical step, which is economical, allowing to perform a plurality of diagnostic tests which use different reaction techniques and a single sample of whole blood which has been subjected to a single pre-analytical treatment, in order to achieve the various reaction phenomena to be studied, both physical, immunological and coagulative.

The Applicant has devised, tested and embodied the present invention to overcome the shortcomings of the state of the art and to obtain these and other purposes and advantages.

SUMMARY OF THE INVENTION

The present invention is set forth and characterized in the relative independent claims, while the dependent claims describe other characteristics of the invention or variants to the main inventive idea.

In accordance with the above purposes, an integrated apparatus for detecting inflammatory states present in a single sample of whole blood and derived from metabolic damage, physical damage or behavioral damage according to the present invention comprises a unit to detect the erythrocyte sedimentation rate (ESR) of the sample of whole blood in order to obtain a preliminary indication of a possible inflammatory state present in said sample. If the value of ESR detected is above normal, it is considered as a sign of probable inflammatory states present in the sample.

The apparatus also comprises a first dispensing unit suitable to dispense a predetermined amount of said sample to at least a pre-treatment unit suitable to perform a pre-treatment in order to substantially eliminate the content of red corpuscles in at least a part of said sample.

The apparatus further comprises a second dispensing unit suitable to dispense a predetermined amount of said part of the sample pre-treated in the pre-treatment unit to one first reactor of a reaction group able to perform at least an immunological and/or coagulative reaction between said predetermined amount of the sample and a latex dispensed in a predetermined amount to the reactor by a third dispensing unit, said latex being suitably sensitized so as to cause said immunological reaction.

Moreover, the apparatus features optical means to measure the kinetics of the immunological and/or coagulative reaction which, advantageously according to a previously memorized calibration curve, allows to measure the concentration of the analyte sought and is therefore indicative of an inflammatory state in the blood sample.

According to one embodiment, the first dispensing unit comprises first microvalve means suitable to dispense said predetermined amount of the sample and first photometric sensing means suitable to detect the volume of said predetermined amount of the sample.

According to another embodiment, the second dispensing unit comprises second microvalve means suitable to dispense said predetermined amount of said part of the sample pre-treated in the pre-treatment unit and second photometric sensing means suitable to detect the dispensed volume of said predetermined amount of said sample pre-treated in the pre-treatment unit.

According to a further embodiment, the third dispensing unit comprises third microvalve means suitable to dispense the predetermined amount of the latex and third photometric sensing means suitable to detect the dispensed volume of said predetermined amount of the latex.

According to a variant, the apparatus comprises a command and control unit at least suitable to coordinate the functioning of the second dispensing unit and of the third dispensing unit in order to maintain the value of the ratio of the dispensed predetermined amount of the sample pre-treated in the pre-treatment unit to the dispensed predetermined amount of the latex in a determined range, correlated to the kind of immunological and/or coagulative reaction.

In one embodiment of the invention, the pre-treatment unit comprises a lysis reactor able to achieve a lysis reaction of a part of said sample in order to obtain a lysed sample. According to this embodiment, the unit to detect the erythrocyte sedimentation rate ESR is also able to measure the equivalent hematocrit factor of the sample of whole blood, to subsequently use this value as a correction factor for the concentrations of the various analytes determined through the specific kinetics which involve the lysed sample. In this way, advantageously, we obtain the concentrations of the various analytes corresponding to the standard concentrations, performed on plasma or serum in the state of the art.

In an alternative embodiment of the invention, the pre-treatment unit comprises a centrifuge device able to centrifuge a part of said sample in order to obtain a centrifuged sample wherein the corpuscular part of the blood is separated from the liquid one, in particular red corpuscles are separated from the whole blood.

According to one embodiment of the invention, the reaction group comprises one or more reactors chosen from a group of reactors comprising:
  a first reactor, in which a first reaction is performed between a first portion of the pre-treated sample and a first latex sensitized with an anti C-reactive protein antibody;
  a second reactor, in which a second reaction is performed between a second portion of the pre-treated sample and a second latex sensitized with a hemolysin, such as streptolysin "O";
  a third reactor, in which a third reaction is performed between a third portion of the pre-treated sample and a third latex sensitized for the antigen-antibody reaction due to a macroglobulin whose presence is connected to the rheumatoid factor RF;
  a fourth reactor, in which a fourth reaction is performed between a fourth portion of the pre-treated sample and a fourth latex comprising an anti-fibrinogen antibody, in order to measure the content of fibrinogen in the sample of whole blood.

According to a variant of the invention, the fourth reactor is also able to perform at least a coagulation reaction between a part of said sample and a coagulation reagent. In this case, the third dispensing unit is also able to dispense a predetermined amount of the coagulation reagent to the coagulation reactor, the command and control unit also being able to maintain the ratio of said part of said sample or the dispensed predetermined amount of the sample pre-treated in the pre-treatment unit to the dispensed predetermined amount of the coagulation reagent in a determined range, correlated to the coagulation reaction.

The apparatus is advantageously fully managed by the aforementioned command and control unit, which further commands and controls the detection unit, the reaction group and the optical means, processing the data received in order to generate information, available for an operator, on the state of inflammation of the sample of whole blood.

Advantageously, the apparatus according to the invention functions effectively as a single analytical point and allows to carry out a plurality of diagnostic tests, which use different reaction techniques and different quotas of whole blood, deriving from a single sample of whole blood which has been subjected to a single pre-analytical treatment, in order to achieve the different reactions to be studied, both physical, immunological and coagulative.

The apparatus according to the present invention has the further advantage that is successfully applicable to the analysis of immunological and/or coagulative reactions, which involve a very strict control of the quantity of the part of the sample and of the quantity of the reagent that are subjected to the reactions, these latter quantities further varying according to the kind of reaction.

According to the present invention, a method for detecting inflammatory states present in a single sample of whole blood and derived from metabolic damage, physical damage or behavioral damage comprises the steps of:
  measuring the value of the erythrocyte sedimentation rate ESR of said sample, in order to obtain a preliminary indication of a possible inflammatory state present in said sample;
  subjecting to a pre-treatment, in a pre-treatment unit, a part of said sample in order to substantially eliminate the influence of red corpuscles, wherein a predetermined amount of said sample is dispensed to the pre-treatment unit by using a first dispensing unit;
  performing at least an immunological and/or coagulative reaction between a predetermined amount of said part of the sample pre-treated in the pre-treatment unit and a latex, by using a first reactor of a reaction group, said latex being suitably sensitized so as to cause said immunological reaction; wherein the predetermined amount of the pre-treated sample is dispensed to the first reactor by using a second dispensing unit and wherein the latex is dispensed to said first reactor by using a third dispensing unit;
  measuring at least the kinetics of said reaction, indicative of said inflammatory states present in said sample.

According to a variant of the invention, the method also comprises the step of measuring the value of the equivalent hematocrit factor of said sample; in this case the pre-treating step comprises a lysis reaction step of a part of said sample in order to obtain a lysed sample and further comprises the step of correcting the measurement of the kinetics of said reaction performed with the portion of lysed sample, by means of said equivalent hematocrit factor.

According to another variant of the invention the pre-treating step comprises a centrifuge step in order to obtain a centrifuged sample wherein the corpuscular part of the blood is separated from the liquid one, in particular the red corpuscles are separated from the whole blood.

According to a further embodiment, the method also comprises a step of performing at least a coagulation reaction between a part of said sample or a portion of the sample pre-treated in the pre-treatment unit and a coagulation reagent, by using a coagulation reactor of the reaction group and measuring at least the kinetics of the coagulation reaction; wherein a predetermined amount of the coagulation reagent is dispensed to the coagulation reactor by using the third dispensing unit.

The method according to the invention allows to carry out a plurality of diagnostic tests, which use different reaction techniques and different quotas of whole blood, deriving from a single sample of whole blood which has been subjected to a single pre-analytical treatment. The method is thus economical and reliable, and reduces the possibility of errors due to the different pre-analytical steps of the state of the art.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 1:
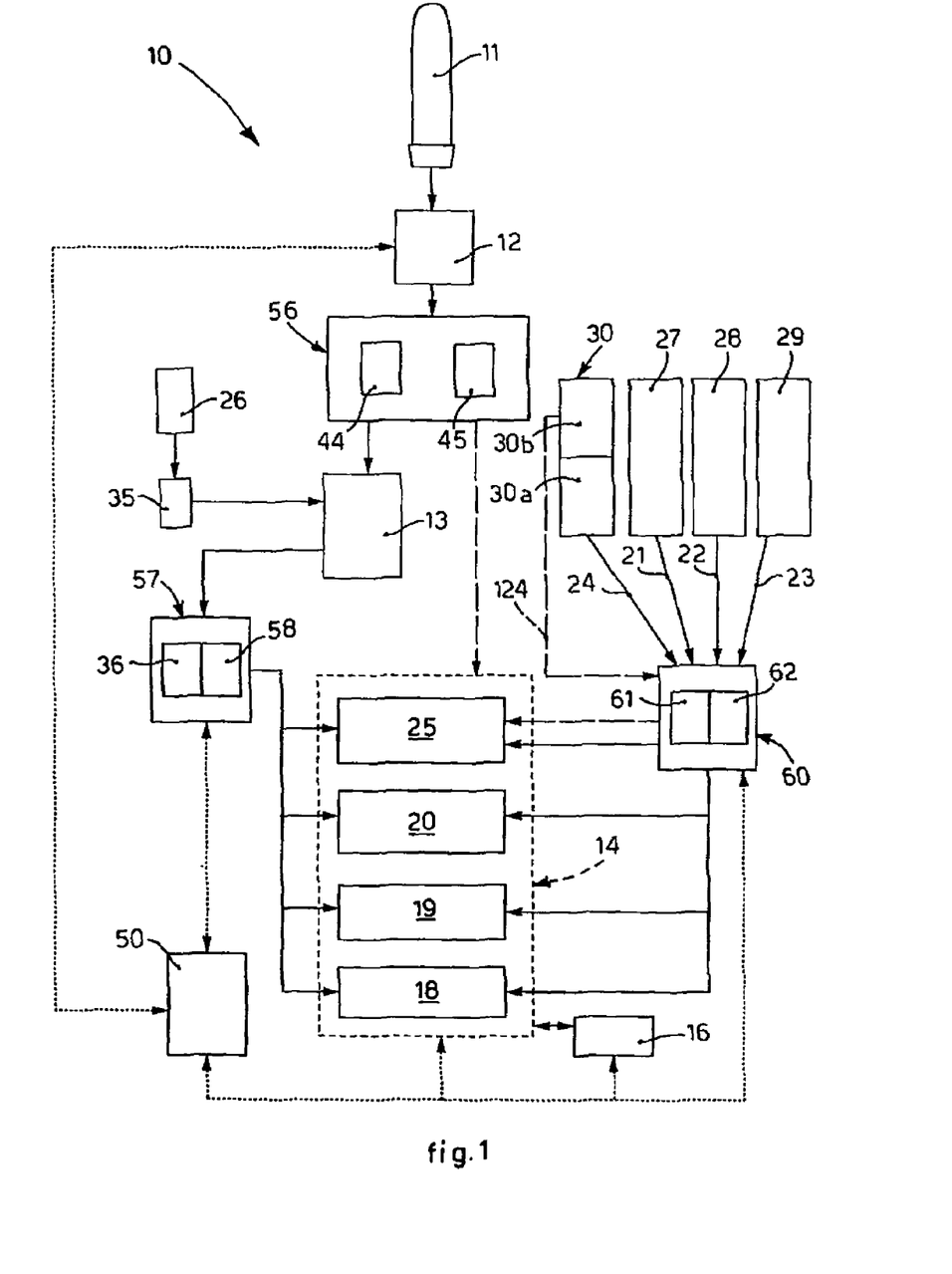
FIG. 1 is an overall schematic representation of an apparatus according to the present invention.

In accordance with the present invention, FIG. 1 shows an integrated apparatus 10 for detecting inflammatory states present in a sample 11 of whole blood.

The apparatus 10 comprises an analyzer 12 to analyze the erythrocyte sedimentation rate ESR, for example as in EP'188, which is provided with a micro calculator that coordinates all the analytical operations, that is, homogenization of the samples, picking up the sample, analytical measurement of the sample, discharge of sample.

Figure 2:
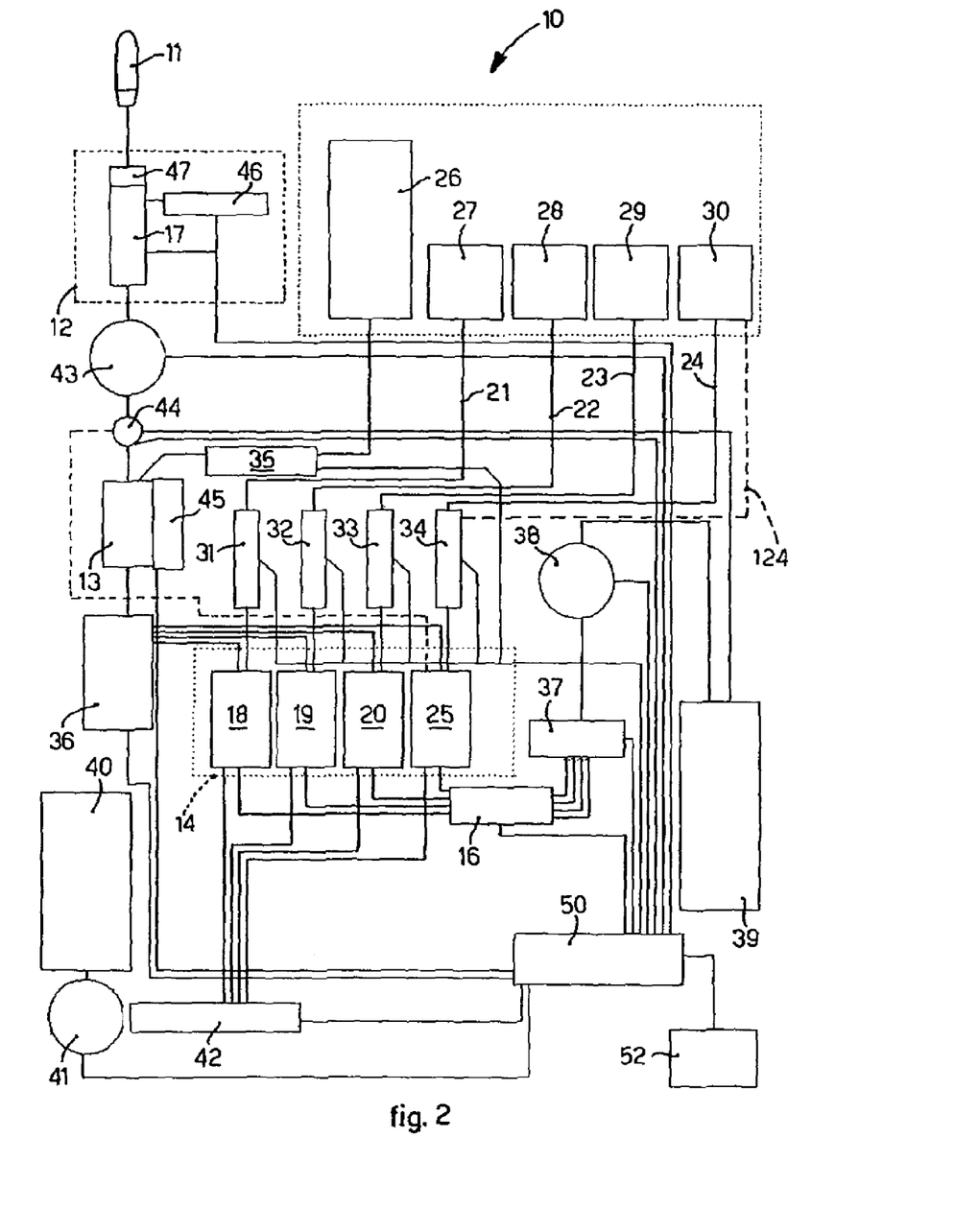
FIG. 2 is a detailed schematic representation of the apparatus in FIG. 1.

The analyzer 12 comprises a loader 47 to load the blood samples and an agitator 46 to agitate the blood samples (FIG. 2).

Each blood sample 11 is identified by means of its own bar code, or an RFID tag, which carries information on the sample and on the treatment to be done, and which can be read by a suitable bar code reader or RFID reader.

The analyzer 12 comprises a CPS type device 17 consisting of a microphotometer and a capillary where the stopped flow is done, so as to measure the kinetics of optical density of the blood and to read the relative syllectogram.

The analyzer 12 is commanded and controlled by a command and control unit 50 which also calculates the parameters of the syllectogram, the erythrocyte sedimentation rate ESR and the anemia factor which is correlated to the equivalent hematocrit value, as described in the patent application UD2006000111 in the name of the present Applicant.

The data processed by the command and control unit 50 on the state of inflammation of the sample of whole blood are available to an operator, for example by means of a printer 52.

Moreover, a sealed device is provided for taking the blood sample, equipped with a pump 43 for moving the blood sample, downstream of the microphotometer.

When the measurement of the ESR is complete, part of the sample used, about 10 microliters, is sent by the pump 43 and a subsequent first dispensing unit 56 to a pre-treatment unit 13, where a pre-treatment occurs in order to substantially eliminate the influence of the red corpuscles, that is to reduce or eliminate their masking effect on the subsequent analysis.

The first dispensing unit 56 is provided with first primary control microvalve 44 in order to regulate the flow rate at outlet from the pump 43, the microvalve 44 being electrically commanded by the command and control unit 50 and allows to dose volumes of about 10 nanoliters per pulse.

The technical characteristics of the first microvalve 44 allow to deliver 1000 drops per second.

By varying the number of total pulses the total volume delivered is easily varied and controlled.

The dispensing unit 56 is further provided with a photometric system 45 that optically controls the outlet of the first microvalve 44 that delivers the volume of blood to the pre-treatment unit 13. The photometric system 45 counts the drops actually delivered by the microvalve 44, thus determining the volume actually dispensed. The optical reader is tuned to 540 nm, which corresponds to the average color of hemoglobin, contained in the red corpuscles.

According to one embodiment, the pre-treatment unit 13 is a lysis reactor of the known type, using chemical lysant well known in the art.

The mass of the lysis reactor, thermostated to 37° C., is big enough not to be subjected to appreciable variations in temperature (±1° C.) due to the addition of the blood sample and the volume of chemical lysant, kept at environmental temperature (25° C.).

The chemical lysant can also perform the function of dilutant so as to calibrate the proper concentration of the blood sample in order to achieve the subsequent immunological reaction.

In the lysis reactor a sufficient quantity of material is distributed so as to be able to perform the different immunological reactions of the same blood sample 11, that is, the test for C-reactive protein, the ASO test and the RF test.

The indicative dilution ratio is about 1/10, that is, one volume of blood sample 11 and nine volumes of chemical lysant.

The chemical lysant is picked up by means of a dispenser equipped with a microvalve 35 from a lysant tank 26.

The two microvalves 35 and 44 work in coordination so as to promote the mixing of the two liquids, with advantageous mixing results when the total delivery time coincides, that is, having established the volume that the two microvalves have to deliver, which can even be very different between the two, the delivery time will be the same for each microvalve and therefore, their flow rate will vary.

Advantageously, the two microvalves 35 and 44 are oriented so as to deliver the liquids at a single common point, called focus of delivery.

Advantageously, the same lysed sample can be used to perform a coagulation test, since the substances used in coagulation tests are unchanged.

According to an alternative embodiment, the pre-treatment unit 13 is a centrifuge device able to centrifuge a part of said sample in order to separate the corpuscular part of the blood from the liquid one.

The apparatus 10 also comprises an analyzer of immunological reactions 14, disposed downstream of the pre-treatment unit 13.

The analyzer of immunological reactions 14 comprises a plurality of reactors 18, 19, 20, 25.

The outlet of the pre-treatment unit 13 is connected, through a capillary, to a subsequent second dispensing unit 57 that is able to selectively dispense a part of the pre-treated sample to one or more of the reactors 18, 19, 20, 25.

The corresponding reagents are dispensed to the relative one of the reactors 18, 19, 20, 25 by a third dispensing unit 60, provided with a microvalve group 61 and photometer sensing group 62 in order to control and detect the dispensed volume of the reagents.

In particular, the second dispensing unit 57 is provided with a mobile microvalve 36, analogous to the microvalves 35 and 44, the function of which is to deliver the volumes necessary to the selected one of the reactors 18, 19, 20, 25 to perform the immunological reactions in the relative reactors.

A motorized system moves the microvalve 36 carrying the pre-treated sample from the initial washing and priming position to the mixing position, in correspondence with the selected reactor 18, 19, 20, 25.

A first part of the pre-treated sample is thus injected from the microvalve 36 into a first reactor 18 for the analysis of the C-reactive protein, the quantity of the injection being controlled by a photometric system 58 analogous to the photometer 45.

In the first reactor 18 occurs a first immunological reaction between the first part of the pre-treated sample and a first latex 21, comprising an anti C-reactive protein antibody.

The first latex 21 is dispensed from a first tank 27 by means of the third dispensing unit 60 inside the first reactor 18. In particular, the microvalve group 61 of the third dispensing unit 60 is provided with a first microvalve dispenser 31 comprising two microvalves, not shown in the drawings: the function of the first is to start the specific reaction, adding an adequate volume of the first sensitized latex 21, and the second, when the concentration of the sample analyzed exceeds a determinate threshold of concentration, allows to perform a second reaction with a greater dilution of the sample, delivering a determinate quantity of buffer to prevent the hook effect, which is typical in this type of reaction.

According to an advantageous form of embodiment, the first tank 27 of the first latex 21 is kept in a thermostated cell, for example with Peltier cells at about 4-8° C., so as not to compromise the effectiveness thereof.

Figure 3:
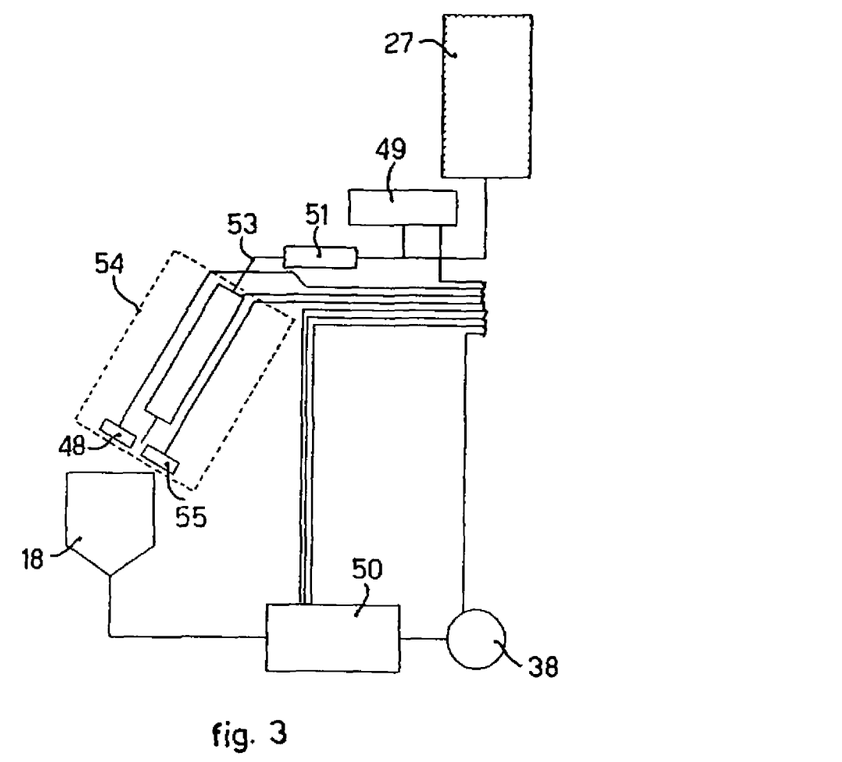
FIG. 3 is a schematic representation of a part of the apparatus in FIG. 1.

The first latex 21 is picked up from the first tank 27 by the terminal part of a capillary 53. This latter and the first dispenser 31 are thermostated at 37° C. by a thermostat 51, so as to deliver the volume of reagent necessary for the reaction at a standardized temperature of 37° C.±1 (FIG. 3).

The pressure of the first latex 21 in the circuit is controlled by a sensor pressure 49.

Moreover, the photometer sensing group 62 comprises a photometer 54 that optically controls the dispensation of the first latex 21, equipped with an emitter 48 and a receiver 55 which, in substance, counts the drops actually delivered, just like the photometric system 45 described above (FIG. 3).

The homogeneity of the latex reagent for the immunological reaction is ensured by a vortex type system which is put into action before starting the analytical cycle.

When the specific immunological reaction has started, a multichannel photometer 16 measures the kinetics and the command and control unit 50 determines the parameters of the reaction according to a memorized calibration curve.

This latter is constructed by determining samples with a known concentration and serves to connect the value of the kinetics measured by the photometer 16 to the efficiency of the latex or reagent used.

The volumes and volume ratios that the microvalves and the dispensers can deliver can be varied according to a determinate algorithm present in the command and control unit 50.

The analyzer of immunological reactions 14 also comprises a second reactor 19, in which a second reaction occurs between a second part of the pre-treated sample and a second latex 22 comprising a hemolysin, such as the streptolysin "O", so as to perform the ASO test.

A third reactor 20 is also provided, where a third reaction takes place between a third part of the pre-treated sample and a third latex 23 comprising an antigen of human gamma globulin IgG for the RF test.

The second reactor 19 and the third reactor 20 of immunological reactions operate in the same way and are provided with the solutions as described above for the first reactor 18, to control dispensation, microvalve 36 and photometer 58 of second dispensing unit 57, and thermostating, and differ in the type of latex 22 or 23, sensitized specifically for the immunological reaction sought. The latex 22 and 23 are dispensed by corresponding second and third microvalve dispensers 32, 33 of the microvalve group 61 of the third dispensing unit 60, connected to respective tanks 28, 29. The dispensed volumes are detected by using photometers of the photometer sensing group 62, analogous to photometer 54. The second and third immunological reactions are analyzed by the photometer 16 exactly as already described for the first reaction.

According to a variant, the analyzer of immunological reactions 14 also comprises a fourth reactor 25, to measure the level of fibrinogen in the blood.

According to one embodiment, the fourth reactor 25 is able to perform a fourth immunological reaction, the kinetics of which is measured by the photometer 16 in the same way, between a fourth part of the pre-treated sample and a fourth latex 24, comprising an anti-fibrinogen antibody, dispensed by a fourth microvalve dispenser 34 of the microvalve group 61 of the third dispensing unit 60, connected to a tank 30, in particular to a part 30a of the tank 30 where the fourth latex 24 is stocked.

According to another embodiment, the fourth reactor 25 is also able to perform a coagulation reaction between a part of said sample and a coagulation reagent 124.

In this case, the fourth latex 24 is not used, but a volume of the primary sample 11, not pre-treated, is mixed, fed by the first microvalve 44, shown by an arrow of dashes in FIGS. 1 and 2, with an adequate volume of coagulation reagent 124 which causes the coagulation phenomenon, such as thrombin, prothrombin or thromboplastin, suitably dispensed from the fourth microvalve dispenser 34 connected to the tank 30, in particular to a part 30b of the tank 30 where the coagulation reagent 124 is stocked.

The coagulation reagent 124 is kept thermostated at 4-8° C. using Peltier cells.

The sample of whole blood necessary for the coagulation reaction is delivered into the fourth reactor 25, after the ERS has been measured, using the first microvalve 44.

In this case too, the terminal part of the capillary, which picks up the reagent from the tank, is thermostated at 37° C. and the reagent is homogenized by means of a vortex type system, which is put into action before the analytical cycle is started.

The photometer 16 measures the coagulation kinetics and the command and control unit 50 determines the parameters of the reaction according to a memorized calibration curve, constructed in the same way previously described.

Having detected the initial state of the coagulation reaction, when the compounds of the reaction, percentage-wise, are still in the liquid state, the photometer 16 enables a washing cycle that restores the initial conditions of each reactor 18, 19, 20, 25.

The washing circuit comprises a tank for the washing liquid 40 and a pump for the washing liquid 41 which cooperates with a valve to control the washing 42.

At outlet from the photometer 16 there is a control collector of the discharge 37, connected to a discharge pump 38 which delivers at outlet to a discharge tank 39.

According to another variant, a multicell system of the microplate type is achieved, of the standardized type with 96 or 192 cells, in which the individual lysis reactions are performed and subsequently, in the same cells, the immunological or coagulation reactions.

Advantageously, the apparatus 10 uses a single sample 11 of whole blood, usually used to measure the blood count or corpuscle count, in order to perform, in the same instrument, different diagnostic tests to confirm an inflammatory state.

Advantageously, the determination of the concentrations of the substances sought is equivalent to the determination performed on blood serum and plasma, standardizing the values measured thanks to the use of the photometrical values correlated to the value of the equivalent hematocrit factor, without needing to adopt a system to measure the hematocrit, which is a typical measurement of corpuscle counts or of centrifugal systems.

Figure 4:
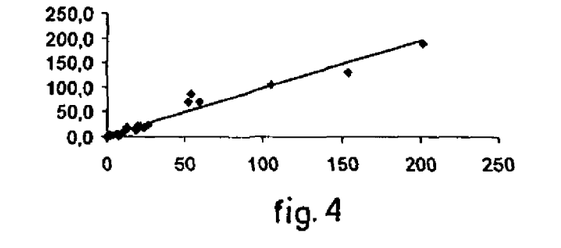
FIG. 4 is a diagram comparing the data of a CRP test measured by means of the apparatus in FIG. 1, values on the y axis, and measured by means of the known reference method, values on the x axis.
Figure 5:
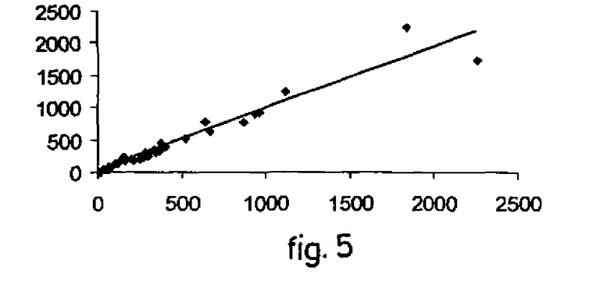
FIG. 5 is a diagram comparing the data of an ASO test measured by means of the apparatus in FIG. 1, values on the y axis, and measured by means of the known reference method, values on the x axis.
Figure 6:
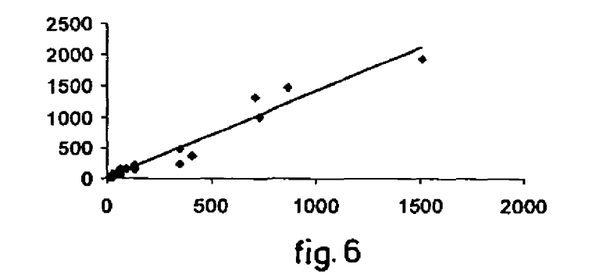
FIG. 6 is a diagram comparing the data of an RF test measured by means of the apparatus in FIG. 1, values on the y axis, and measured by means of the known reference method, values on the x axis.

In fact, in FIGS. 4, 5 and 6, we can see the correlation between the data obtained using known methods (gold standard), respectively for the CRP test in mg/l, the ASO test and the RF test in UI/ml, shown on the x axis, and the values obtained with the present invention for said tests, shown on the y axis.

The correlation factors of said tests are equal, respectively, to 0.982, 0.9698 and 0.975, showing the efficiency of the experimentation done.

Advantageously, moreover, the reaction time is reduced by using concentrated reagents.

In fact, it is possible to use concentrated reagents by exploiting a measurement cell of the photometer 16 with a short optical path, comprised between about 0.4 and 0.9 mm, advantageously between about 0.6 and 0.8 mm, which allows the photometer to work in the ideal measuring range, comprised between about 20% and 80% transmittance, where the relative error is less than 2%.

The use of this greater concentration of reagents allows to perform and measure the immunological reaction in a relatively shorter time, comprised between about 0.5 and 6 minutes, advantageously between about 0.5 and 2 minutes.

Advantageously, the consequent size of the measuring cell and the optical path allows to achieve reactions with overall volumes comprised between 2-3 microliters, as opposed to the 700-800 microliters or even more in the state of the art.

It is clear that modifications and/or additions of parts may be made to the apparatus and method for detecting inflammatory states present in a sample of whole blood as described heretofore, without departing from the scope of the present invention.

The invention claimed is:

1. An integrated apparatus for detecting inflammatory states present in a single sample of whole blood and derived from metabolic damage, physical damage or behavioral damage, the apparatus comprising:

a detection unit to detect the erythrocyte sedimentation rate (ESR) of said sample, in order to obtain a preliminary indication of a possible inflammatory state present in said sample;

a first dispensing unit connected downstream of said detection unit, the first dispending unit comprising a first microvalve suitable to dispense a predetermined amount of said sample at least to a pre-treatment unit suitable to perform a pre-treatment in order to substantially eliminate the content of red corpuscles in at least a part of said sample subjected to detection of the erythrocyte sedimentation rate (ESR);

a second dispensing unit connected downstream to said pre-treatment unit, the second dispensing unit comprising a second microvalve suitable to dispense a predetermined amount of said part of the sample pre-treated in the pre-treatment unit to each of a plurality of reactors of a reaction group for performing at least an immunological and/or coagulative reaction between said predetermined amount of the sample and each of a plurality of latexes dispensed in a predetermined amount to each of the reactors by a third dispensing unit, each of said latexes being suitably sensitized so as to cause said immunological and/or coagulative reaction, wherein the plurality of reactors includes a reactor for reacting a portion of said predetermined amount of the sample pre-treated in the pre-treatment unit and one of the latexes comprising an anti C-reactive protein antibody, and another reactor for reacting another portion of said predetermined amount of the sample pre-treated in the pre-treatment unit and another one of the latexes sensitized to detect a rheumatic factor; and an optical device able to measure the kinetics of said immunological and/or coagulative reaction, indicative of said inflammatory states present in said sample.

2. The apparatus as in claim 1, wherein said first dispensing unit comprises a first photometric sensing device suitable to detect the volume of said predetermined amount of the sample.

3. The apparatus as in claim 1, wherein said second dispensing unit comprises a second photometric sensing device suitable to detect a dispensed volume of said predetermined amount of said sample pre-treated in the pre-treatment unit.

4. The apparatus as in claim 1, wherein said third dispensing unit comprises a third microvalve suitable to dispense the predetermined amount of each of the latexes and a third photometric sensing device suitable to detect a dispensed volume of said predetermined amount of each of the latexes.

5. The apparatus as in claim 1, further comprising a command and control unit at least suitable to coordinate a functioning of the second dispensing unit and of the third dispensing unit in order to maintain a value of a ratio of a dispensed predetermined amount of the sample pre-treated in the pre-treatment unit to a dispensed predetermined amount of the latex in a determined range, correlated to a kind of the immunological and/or coagulative reaction.

6. The apparatus as in claim 1, wherein said pre-treatment unit comprises a lysis reactor able to achieve a lysis reaction of a part of said sample in order to obtain a lysed sample.

7. The apparatus as in claim 1, wherein said pre-treatment unit comprises a centrifuge device able to centrifuge a part of said sample in order to obtain a centrifuged sample wherein the red corpuscles are separated from the whole blood.

8. The apparatus as in claim 1, wherein said detection unit is also able to measure the equivalent hematocrit factor of said sample.

9. The apparatus as in claim 1, further comprising a coagulation reactor of the reaction group able to perform at least a coagulation reaction between a part of said sample and a coagulation reagent.

10. The apparatus as in claim 9, wherein the third dispensing unit is also able to dispense a predetermined amount of the coagulation reagent to the coagulation reactor, a command and control unit being able to maintain a ratio of said part of said sample or a dispensed predetermined amount of the sample pre-treated in the pre-treatment unit to a dispensed predetermined amount of the coagulation reagent in a determined range, correlated to the coagulation reaction.

11. The apparatus as in claim 1, wherein said reaction group comprises an additional reactor for reacting an additional portion of said predetermined amount of the sample pre-treated in the pre-treatment unit and an additional one of the latexes comprising streptolysin "O".

12. The apparatus as in claim 1, wherein said reaction group comprises a fourth reactor, in which a fourth reaction is able to occur between a fourth portion of said predetermined amount of the sample pre-treated in the pre-treatment unit and a fourth latex comprising an anti-fibrinogen antibody, to measure the content of fibrinogen in said sample.

13. The apparatus as in claim 9, wherein said reaction group comprises another reactor, in which a reaction is able to occur between a portion of said sample or a portion of said predetermined amount of the sample pre-treated in the pre-treatment unit and said coagulation reagent.

14. The apparatus as in claim 5, wherein the command and control unit is also able to command and control said detection unit and said reaction group.

15. The apparatus as in claim 1, wherein the optical device comprises a photometer having a measurement cell with an optical path comprised between about 0.4 mm and 0.9 mm.

16. A method for detecting inflammatory states present in a single sample of whole blood and derived from metabolic damage, physical damage or behavioral damage, the method comprising the steps of:
measuring a value of an erythrocyte sedimentation rate (ESR) of said sample, in order to obtain a preliminary indication of a possible inflammatory state present in said single sample;
producing a pre-treated sample by subjecting to a pre-treatment, in a pre-treatment unit, a part of said single sample subjected to measurement of the value of the erythrocyte sedimentation rate (ESR) in order to substantially eliminate a content of red corpuscles, wherein a predetermined amount of said single sample subjected to measurement of the value of the erythrocyte sedimentation rate (ESR) is dispensed to the pre-treatment unit by using a first dispensing unit comprising a microvalve suitable to dispense said predetermined amount of said sample subjected to measurement of the value of the erythrocyte sedimentation rate (ESR) to the pre-treatment unit;
performing an immunological and/or a coagulative reactions between a predetermined amount of the pre-treated sample and a plurality of latexes, by using a plurality of reactors of a reaction group, wherein portions of the predetermined amount of the pre-treated sample is dispensed to each of the reactors by using a second dispensing unit comprising a second microvalve suitable to dispense said portions of the predetermined amount of the pre-treated sample to each of the reactors, and wherein each of the latexes is dispensed by using a third dispensing unit, wherein the performing step includes reacting in one of the reactors one of the portions of the predetermined amount and one of the latexes comprising an anti C-reactive protein antibody, and reacting in another one of the reactors another one of the portions of the predetermined amount and another one of the latexes sensitized to detect a rheumatic factor; and
measuring at least the kinetics of said reaction, indicative of said inflammatory states present in said sample.

17. The method as in claim 16, further comprising:
measuring a value of an equivalent hematocrit factor of said sample, wherein the pre-treatment includes a lysis reaction step of a part of said sample in order to obtain a lysed sample; and
correcting a measurement of a kinetics of said reaction performed with a portion of the lysed sample, by said equivalent hematocrit factor.

18. The method as in claim 16, wherein the pre-treatment includes a centrifuge step in order to obtain a centrifuged sample wherein the red corpuscles are separated from the whole blood.

19. The method as in claim 16, further comprising:
performing at least a coagulation reaction between a part of said sample or a portion of the sample pre-treated in the pre-treatment unit and a coagulation reagent, by using a coagulation reactor of the reaction group, wherein a predetermined amount of the coagulation reagent is dispensed by using the third dispensing unit.

20. The method as in claim 16, further comprising: maintaining a ratio of a dispensed predetermined amount of the sample pre-treated in the pre-treatment unit to a dispensed volume of each of the latexes in a determined range, correlated to a kind of the immunological and/or coagulative reaction, by using a command and control unit.

21. The method as in claim 20, further comprising: maintaining a ratio of said part of said sample or said portion of the sample pre-treated in the pre-treatment unit to a dispensed predetermined amount of a coagulation reagent in a determined range, correlated to a coagulation reaction, by using the command and control unit.

* * * * *